(12) United States Patent
Tian et al.

(10) Patent No.: US 11,155,514 B1
(45) Date of Patent: Oct. 26, 2021

(54) PLEUROMULIN ACITRETIN ESTER WITH ANTIBACTERIAL ACTIVITY AND A METHOD OF PREPARING THE SAME

(71) Applicants: Bin Tian, Xi'an (CN); Juan Li, Xi'an (CN); Nan Hui, Xi'an (CN); Guaiping Qiao, Xi'an (CN); Liang Xin, Xi'an (CN); Jingyi Li, Xi'an (CN); Dan Yang, Xi'an (CN); Han Li, Xi'an (CN); Yanjun Li, Xi'an (CN); Liang Qi, Xi'an (CN); Wenbo Yao, Xi'an (CN); Chengyuan Liang, Xi'an (CN)

(72) Inventors: Bin Tian, Xi'an (CN); Juan Li, Xi'an (CN); Nan Hui, Xi'an (CN); Guaiping Qiao, Xi'an (CN); Liang Xin, Xi'an (CN); Jingyi Li, Xi'an (CN); Dan Yang, Xi'an (CN); Han Li, Xi'an (CN); Yanjun Li, Xi'an (CN); Liang Qi, Xi'an (CN); Wenbo Yao, Xi'an (CN); Chengyuan Liang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 17/128,102

(22) Filed: Dec. 19, 2020

(51) Int. Cl.
*C07C 69/736* (2006.01)
*C07C 67/56* (2006.01)
*C07C 67/08* (2006.01)

(52) U.S. Cl.
CPC ............ *C07C 69/736* (2013.01); *C07C 67/08* (2013.01); *C07C 67/56* (2013.01); *C07C 2603/82* (2017.05)

(58) Field of Classification Search
None
See application file for complete search history.

(56) References Cited

U.S. PATENT DOCUMENTS

| RE39,128 E  * | 6/2006  | Berry ................. C07D 211/20 514/305 |
| RE43,390 E  * | 5/2012  | Berry ................. C07D 453/02 514/305 |
| 10,836,703 B1 * | 11/2020 | Wang ....................... C07C 69/52 |
| 11,084,775 B1 * | 8/2021  | Tian ........................ C07C 67/08 |

OTHER PUBLICATIONS

Li ("Nucleophilic trifluoromethoxylation of alkyl halides without silver" Nature Communications, 2020, (11)755) (Year: 2020).*
RN1217455-80-5 (STN registry file, publicly available since Apr. 8, 2010) (Year: 2010).*

* cited by examiner

*Primary Examiner* — Amy C Bonaparte

(57) ABSTRACT

A compound with anti-drug resistant bacteria activity having the following formula (I)

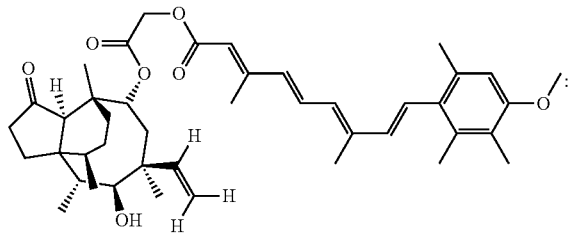

(I) is disclosed. A method of preparing the compound of formula (I) is also disclosed.

15 Claims, 1 Drawing Sheet

PLEUROMULIN ACITRETIN ESTER WITH ANTIBACTERIAL ACTIVITY AND A METHOD OF PREPARING THE SAME

FIELD OF THE INVENTION

The present invention relates to the field of medicinal chemistry, and in particular, to a pleuromulin acitretin ester with anti-drug-resistant-bacteria activity and a method of preparing the same.

BACKGROUND OF THE INVENTION

Multi-drug resistant bacteria mainly refer to bacteria that are resistant to three or more types of antibacterial drugs used in clinical practice. The emergence and prevalence of multi-drug-resistant bacteria bring huge challenges to clinical treatment in the 21st century. At present, both gram-positive and negative bacteria have resistance trends, including methicillin-resistant *Staphylococcus aureus* (MRSA), penicillin-resistant *Streptococcus pneumoniae* (PRSP), vancomycin-resistant *Enterococcus* (VRE), and extended spectrum β-lactamase (ESBI), multi-drug resistant tuberculosis (MDRMT), etc. Among them, the drug resistance of gram-positive bacteria is more serious. Faced with the challenges posed by multi-drug resistant bacteria, the development of new anti-drug resistant bacteria drugs is imminent.

Pleuromulin (also known as Pleuromutilin) is an antibiotic produced by submerged culture of the higher fungi basidiomycetes pleurots mutilus and plenrots passeckerianus, and belongs to diterpenoids. The main skeleton is composed of five-membered six-membered and eight-membered rings. Pleuromulin and its derivatives can inhibit the synthesis of bacterial protein at the ribosome level, and have a unique effect on many Gram-positive bacteria and *Mycoplasma* infections.

Acitretin is a synthetic analogue of aromatic vitamin A and an active metabolite of etretinate. It is used to treat severe psoriasis, keratinization diseases and other skin diseases, and is an important medical product.

In the present invention, pleuromulin is modified by the acitretin structure to obtain a pleuromulin acitretin ester. Preliminary antibacterial activity experiment shows the compound has excellent antibacterial activity and has high medical research and application value in the treatment of infectious diseases caused by multidrug resistant bacteria.

SUMMARY OF THE INVENTION

In one embodiment, the present invention provides a pleuromulin acitretin ester, i.e., a compound having the following formula (I):

(I)

In another embodiment, the present application provides a method of preparing the compound of formula (I). The method includes: reacting a compound of formula (II) (pleuromulin) with a compound of formula (III) (acitretin) to obtain the compound of formula (I):

(II)

(III)

(I)

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of 4-DMAP under nitrogen atmosphere to obtain a reaction mixture; heating the reaction mixture at 20-40° C. for 4-8 hours; concentrating the reaction mixture and extracting with ethyl acetate to obtain a crude product; and purifying the crude product on a silica gel fresh chromatography column with petroleum ether and ethyl acetate as an eluent to obtain the compound of formula (I).

In another embodiment, the organic solvent is toluene, dichloromethane or acetonitrile.

In another embodiment, the organic solvent is dichloromethane.

In another embodiment, the molar ratio of the compound of formula (II) and the compound of formula (III) is 1:1.2.

In another embodiment, the reaction mixture is heated at 30° C.

In another embodiment, the reaction mixture is heated for 5 hours.

In another embodiment, the eluent is petroleum ether: ethyl acetate=3:1.

In another embodiment, the reaction of the compound of formula (II) with the compound of formula (III) includes the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 20-60° C. for 4-10 hours; placing the reaction mixture in a separating funnel to separate a crude product; purifying the crude product by recrystallization in methanol to obtain the compound of formula (I); and recycling the ionic liquid.

In another embodiment, the ionic liquid is 1-ethyl-3-methylimidazolium tetrachloroferrate, 1-hexyl-3-methylimidazolium tetrafluoroborate or 1-n-butyl-3-methyl-imidazolium hydrogen sulfate.

In another embodiment, the ionic liquid is 1-n-butyl-3-methyl-imidazolium hydrogen sulfate (BMIM $HSO_4$).

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 40° C.

In another embodiment, the reaction mixture is heated for 8 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
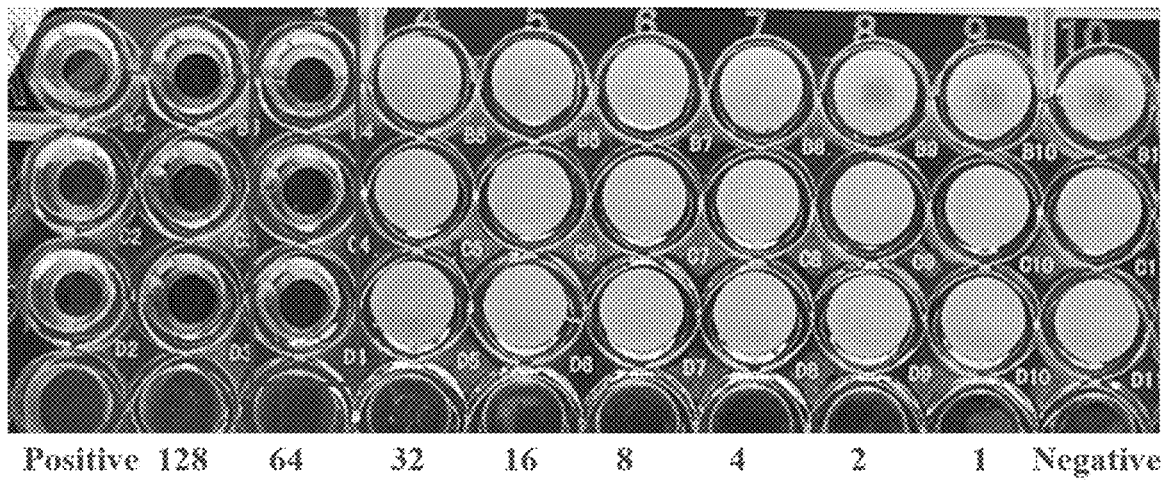
FIG. 1 shows the in vitro antibacterial activity of the pleuromulin acitretin ester against drug-resistant bacteria MRSA 18-575.

Reference will now be made in detail to embodiments of the present invention, example of which is illustrated in the accompanying drawings. The following examples illustrate the present invention, but the present invention is not limited to the following examples.

Example 1

Preparation of the pleuromulin acitretin ester ((2E,4E,6E, 8E)-2-(((4R,5S,6S,8R,9R,9aR,12R)-5-hydroxy-4,6,9,12-tetramethyl-1-oxo-6-vinyldecahydro-3a,9-propanocyclopenta [8]annulen-8-yl)oxy)-2-oxoethyl 9-(4-methoxy-2,3,6-trimethylphenyl)-3,7-dimethylnona-2,4,6,8-tetraenoate)

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of dichloromethane under nitrogen atmosphere. 78.3 mg (0.24 mmol) of acitretin was dissolved in 20 mL of dichloromethane, and added dropwise to the reaction mixture by a separatory funnel. After the completion of the dropwise addition, 206.3 mg (1.00 mmol) of coupling agent DCC (N,N'-dicyclohexylcarbodiimide) was added and the reaction mixture was stirred at 30° C. for 5 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether:ethyl acetate=3:1 as eluent, and the eluent containing the product was combined, concentrated under reduced pressure, and dried to obtain 99.3 mg of the pleuromulin acitretin ester, a total yield of 72.31%.

$^1$H-NMR (400 MHz, chloroform-d) δ (ppm): 7.13 (1H, t), 6.79 (1H, s), 6.68 (3H, t), 6.34 (1H, m), 5.94 (1H, t), 5.87 (1H, d), 5.35 (2H, s), 4.65 (2H, m), 4.19 (1H, m), 3.89 (3H, s), 3.42 (1H, s), 3.02 (1H, d), 2.43 (3H, s), 2.32 (1H, s), 2.30-2.13 (9H, m), 2.14 (3H, s), 2.10 (2H, t), 1.85 (2H, t), 1.73-1.60 (8H, m), 1.45 (3H, d), 0.95-0.82 (9H, s); $^{13}$C-NMR (400 MHz, chloroform-d) (6 ppm): 216.9, 167.1, 165.9, 154.5, 138.8, 133.9, 130.2, 128.8, 122.8, 117.2, 110.0, 74.6, 69.5, 60.8, 58.1, 55.5, 44.6, 41.9, 36.7, 36.0, 34.4, 30.4, 26.8, 26.4, 24.8, 21.4, 17.4, 16.6, 14.8, 14.1, 13.0, 11.8, 11.4.

Example 2

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of toluene under nitrogen atmosphere. 71.8 mg (0.22 mmol) of acitretin was dissolved in 20 mL of toluene, and added dropwise to the reaction mixture by a separatory funnel. After the completion of the dropwise addition, 206.3 mg (1.00 mmol) of coupling agent DCC was added and the reaction mixture was stirred at 40° C. for 4 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether:ethyl acetate=3:1 as eluent, and the eluent containing the product was combined, concentrated under reduced pressure, and dried to obtain 88.4 mg of the pleuromulin acitretin ester, a total yield of 64.37%.

Example 3

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of acetonitrile under nitrogen atmosphere. 78.3 mg (0.24 mmol) of acitretin was dissolved in 20 mL of acetonitrile, and added dropwise to the reaction mixture by a separatory funnel. After the completion of the dropwise addition, 206.3 mg (1.00 mmol) of coupling agent DCC was added and the reaction mixture was stirred at 20° C. for 8 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether:ethyl acetate=3:1 as eluent, and the eluent containing the product was combined, concentrated under reduced pressure, and dried to obtain 87.5 mg of the pleuromulin acitretin ester, a total yield of 63.75%.

Example 4

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of dichloromethane under nitrogen atmosphere. 71.8 mg (0.22 mmol) of acitretin was dissolved in 20 mL of dichloromethane, and added dropwise to the reaction mixture by a separatory funnel. After the completion of the dropwise addition, 206.3 mg (1.00 mmol) of coupling agent DCC was added and the reaction mixture was stirred at 35° C. for 6 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether: ethyl acetate=3:1 as eluent, and the eluent containing the product was combined, concentrated under reduced pressure, and dried to obtain 93.7 mg of the pleuromulin acitretin ester, a total yield of 68.23%.

Example 5

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of toluene under nitrogen atmosphere. 78.3 mg (0.24 mmol) of acitretin was dissolved in 20 mL of toluene, and added dropwise to the reaction mixture by a separatory funnel. After the completion of the dropwise addition, 206.3 mg (1.00 mmol) of coupling agent DCC was added and the reaction mixture was stirred at 30° C. for 5 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether:ethyl acetate=3:1 as eluent, and the eluent containing the product was combined, concentrated under reduced pressure, and dried to obtain 92.2 mg of the pleuromulin acitretin ester, a total yield of 67.14%.

Example 6

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of acetonitrile under nitrogen atmosphere. 71.8 mg (0.22 mmol) of acitretin was dissolved in 20 mL of acetonitrile, and added dropwise to the reaction mixture by a separatory funnel. After the completion of the dropwise addition, 206.3 mg (1.00 mmol) of coupling agent DCC was added and the reaction mixture was stirred at 25° C. for 7 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether:ethyl acetate=3:1 as eluent, and the eluent containing the product was combined, concentrated under reduced pressure, and dried to obtain 89.2 mg of the pleuromulin acitretin ester, a total yield of 64.95%.

Example 7

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of dichloromethane under nitrogen atmosphere. 84.9 mg (0.26 mmol) of acitretin was dissolved in 20 mL of dichloromethane, and added dropwise to the reaction mixture by a separatory funnel. After the completion of the dropwise addition, 206.3 mg (1.00 mmol) of coupling agent DCC was added and the reaction mixture was stirred at 40° C. for 6 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether: ethyl acetate=3:1 as eluent, and the eluent containing the product was combined, concentrated under reduced pressure, and dried to obtain 96.4 mg of the pleuromulin acitretin ester, a total yield of 70.25%.

Example 8

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of toluene under nitrogen atmosphere. 71.8 mg (0.22 mmol) of acitretin was dissolved in 20 mL of toluene, and added dropwise to the reaction mixture by a separatory funnel. After the completion of the dropwise addition, 206.3 mg (1.00 mmol) of coupling agent DCC was added and the reaction mixture was stirred at 20° C. for 8 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether:ethyl acetate=3:2 as eluent, and the eluent containing the product was combined, concentrated under reduced pressure, and dried to obtain 85.3 mg of the pleuromulin acitretin ester, a total yield of 62.17%.

Example 9

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of acetonitrile under nitrogen atmosphere. 71.8 mg (0.22 mmol) of acitretin was dissolved in 20 mL of acetonitrile, and added dropwise to the reaction mixture by a separatory funnel. After the completion of the dropwise addition, 206.3 mg (1.00 mmol) of coupling agent DCC was added and the reaction mixture was stirred at 30° C. for 4 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether:ethyl acetate=3:2 as eluent, and the eluent containing the product was combined, concentrated under reduced pressure, and dried to obtain 87.2 mg of the pleuromulin acitretin ester, a total yield of 63.55%.

Example 10

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of dichloromethane under nitrogen atmosphere. 71.8 mg (0.22 mmol) of acitretin was dissolved in 20 mL of dichloromethane, and added dropwise to the reaction mixture by a separatory funnel. After the completion of the dropwise addition, 206.3 mg (1.00 mmol) of coupling agent DCC was added and the reaction mixture was stirred at 40° C. for 4 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether: ethyl acetate=3:1 as eluent, and the eluent containing the product was combined, concentrated under reduced pressure, and dried to obtain 97.9 mg of the pleuromulin acitretin ester, a total yield of 71.33%.

Example 11

Preparation of the Pleuromulin Acitretin Ester

In a 100 mL three-necked flask, 75.7 mg (0.20 mmol) of pleuromulin and 2.4 mg (0.02 mmol) 4-DMAP (4-(dimethylamino)pyridine) were dissolved in 30 mL of dichloromethane under nitrogen atmosphere. 78.3 mg (0.24 mmol) of acitretin was dissolved in 20 mL of dichloromethane, and added dropwise to the reaction mixture by a separatory funnel. After the completion of the dropwise addition, 206.3 mg (1.00 mmol) of coupling agent DCC was added and the reaction mixture was stirred at 35° C. for 4 hours. Thin layer chromatography was used to track the reaction to completion, heating was stopped, and the protective device was removed. The reaction mixture was concentrated, washed with water, extracted with ethyl acetate, dried and concentrated to give a crude product. The crude product was purified by silica gel column chromatography, eluting with petroleum ether: ethyl acetate=3:2 as eluent, and the eluent containing the product was combined, concentrated under reduced pressure, and dried to obtain 94.1 mg of the pleuromulin acitretin ester, a total yield of 68.54%.

Example 12

Preparation of the Pleuromulin Acitretin Ester

In a 100 mL three-necked flask, 75.7 mg (0.20 mmol) of pleuromulin, 71.8 mg (0.22 mmol) of acitretin and 3.7 mg (0.002 mmol) of silicomolybdic acid were dissolved in 30 mL of 1-n-butyl-3-methylimidazolium hydrogen sulfate under nitrogen atmosphere. After full dissolution, the temperature of the reaction mixture was raised to 40° C., and the reaction was carried out for 8 hours. Thin layer chromatography was used to track the reaction to completion, heating was stopped, and the protective device was removed. The reaction mixture was allowed to separate into layers to give a crude product. The crude product was recrystallized with 20 mL methanol and dried to obtain 116.3 mg of the pleuromulin acitretin ester, a total yield of 84.75%.

Example 13

Preparation of the Pleuromulin Acitretin Ester

In a 100 mL three-necked flask, 75.7 mg (0.20 mmol) of pleuromulin, 71.8 mg (0.22 mmol) of acitretin and 3.7 mg (0.002 mmol) of silicomolybdic acid were dissolved in 30 mL of 1-ethyl-3-methylimidazolium tetrachloroferrate under nitrogen atmosphere. After full dissolution, the temperature of the reaction mixture was raised to 20° C., and the reaction was carried out for 10 hours. Thin layer chromatography was used to track the reaction to completion, heating was stopped, and the protective device was removed. The reaction mixture was allowed to separate into layers to give a crude product. The crude product was recrystallized with 20 mL methanol and dried to obtain 106.7 mg of the pleuromulin acitretin ester, a total yield of 77.75%.

Example 14

Preparation of the Pleuromulin Acitretin Ester

In a 100 mL three-necked flask, 75.7 mg (0.20 mmol) of pleuromulin, 71.8 mg (0.22 mmol) of acitretin and 3.7 mg (0.002 mmol) of silicomolybdic acid were dissolved in 30 mL of 1-hexyl-3-methylimidazolium tetrafluoroborate under nitrogen atmosphere. After full dissolution, the temperature of the reaction mixture was raised to 60° C., and the reaction was carried out for 4 hours. Thin layer chromatography was used to track the reaction to completion, heating was stopped, and the protective device was removed. The reaction mixture was allowed to separate into layers to give a crude product. The crude product was recrystallized with 20 mL methanol and dried to obtain 110.9 mg of the pleuromulin acitretin ester, a total yield of 80.76%.

Example 15

Preparation of the Pleuromulin Acitretin Ester

In a 100 mL three-necked flask, 75.7 mg (0.20 mmol) of pleuromulin, 71.8 mg (0.22 mmol) of acitretin and 3.7 mg (0.002 mmol) of silicomolybdic acid were dissolved in 30 mL of 1-n-butyl-3-methylimidazolium hydrogen sulfate under nitrogen atmosphere. After full dissolution, the temperature of the reaction mixture was raised to 30° C., and the reaction was carried out for 9 hours. Thin layer chromatography was used to track the reaction to completion, heating was stopped, and the protective device was removed. The reaction mixture was allowed to separate into layers to give a crude product. The crude product was recrystallized with 20 mL methanol and dried to obtain 114.7 mg of the pleuromulin acitretin ester, a total yield of 83.55%.

Example 16

Antibacterial Activity Test of the Compounds of the Invention

The minimal inhibitory concentration (MIC) of the compounds was determined by a microbroth dilution method with gentamicin, cefazolin sodium and ceftriaxone sodium as positive controls.

The experimental strains included methicillin-resistant Gram-positive bacteria: methicillin-resistant *Staphylococcus aureus* MRSA 18-222, 18-575; multiple drug-resistant Gram-negative bacteria: vancomycin-resistant enterococci VRE 18-80,18-94, multidrug-resistant *Pseudomonas aeruginosa* MDR-PA 18-174,18-202, carbapenem-resistant *Acinetobacter baumannii* CR-AB 18-183,18-560. All the experimental strains were donated by Huashan Hospital affiliated to Fudan University (Institute of antibiotics, Fudan University) and used after routine identification.

Preparation of Test Strains:

Preparation of MHB medium: 20.0 g MHB medium was added to 1 L distilled water, boiled until completely dissolved, packed in conical bottles and sterilized at 121° C. for 15 min.

The experimental strain was cultured to the logarithmic growth phase: under aseptic condition, the experimental strain was inoculated into 100 mL MHB medium and incubated in a constant temperature and humidity incubator at 37° C. for 20-22 hours.

Preparation of storage solution: weigh the sample to be tested, dissolve it with 1% DMSO solution, prepare a storage solution with a concentration of 2560 µg/mL, weigh a positive reference substance, dissolve it with aseptic distilled water, and configure a storage solution with a concentration of 2560 µg/mL.

Preparation of bacterial suspension: under aseptic condition, the experimental strains cultured to logarithmic growth phase were adjusted to 0.5 MCF turbidity standard with MHB medium and diluted according to 1:10, and the bacterial suspension with concentration of $10^6$ CFU/mL was prepared for standby.

Stock solution dilution and inoculation of experimental strains: under aseptic conditions, dilute the stock solution to a solution of 256 µg/mL. Take a sterile 96-well plate, add 100 µL of MHB medium to each well except for the first and second wells; add 100 µL of positive control solution to the first well, and add 100 µL of compound sample solution to the second and third wells; Mix the sample solution in the 3 wells with the medium, and then pipet 100 µL to the 4th well, and then pipet 100 µL to the 5th well after mixing, and then dilute to the 9th well in a series of times, and draw 100 µL from the 9th well and discard, the 10th well is a growth control without drugs; then, add 100 µL of the above-prepared bacterial suspension to each well to make the final bacterial concentration of each well $5 \times 10^5$ CFU/mL; so far, the positive control concentration is 128 µg/mL, the concentration of the sample solution is 128, 64, 32, 16, 8, 4, 2, 1 µg/mL.

Incubation: Cover the 96-well plate inoculated with the experimental strains, and incubate in a constant temperature and humidity box at 37° C. for 20-22 hours.

Interpretation of the MIC endpoint: The concentration that can completely inhibit the growth of bacteria in a 96-well plate under a black background is the lowest inhibitory concentration of the sample against the bacteria.

Figure 2:
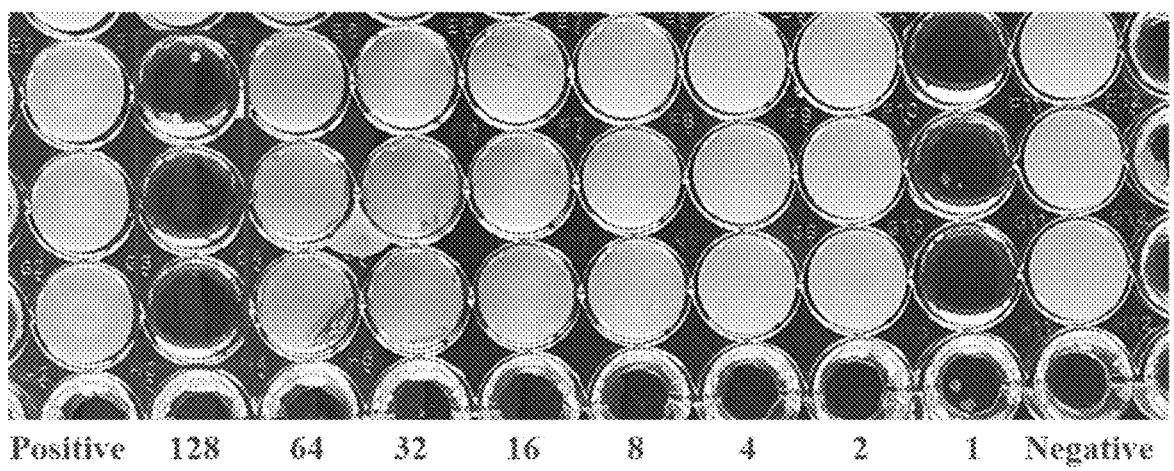
FIG. 2 shows the in vitro antibacterial activity of the pleuromulin acitretin ester against drug-resistant bacteria MDR-PA 18-202.

In FIGS. 1-2, the ten wells represent ten groups, from left to right, positive, 128 µg/mL, 64 µg/mL, 32 µg/mL, 16 µg/mL, 8 µg/mL, 4 µg/mL, 2 µg/mL, 1 µg/mL, Negative. FIG. 1 shows the in vitro antibacterial activity of pleuromulin acitretin ester against drug-resistant bacteria MRSA 18-575. FIG. 2 shows the in vitro antibacterial activity of pleuromulin acitretin ester against drug-resistant bacteria MDR-PA 18-202. The results are shown in Table 1.

According to the experimental results of FIG. 1-2 and Table 1, pleuromulin and acitretin had no inhibitory effect on drug-resistant bacteria, while pleuromulin acitretin ester showed a strong inhibitory effect on multi-drug resistant *Pseudomonas aeruginosa* MDR-PA (MIC=128 µg/mL) and multi-drug resistant *Staphylococcus aureus* MRSA (MIC=64 µg/mL). In summary, the pleuromulin acitretin ester of the present invention can be used as antibacterial drug candidates for multidrug resistant *Pseudomonas aeruginosa* and multidrug resistant *Staphylococcus aureus*, as well as further preclinical research.

What is claimed is:

1. A compound having the following formula (I):

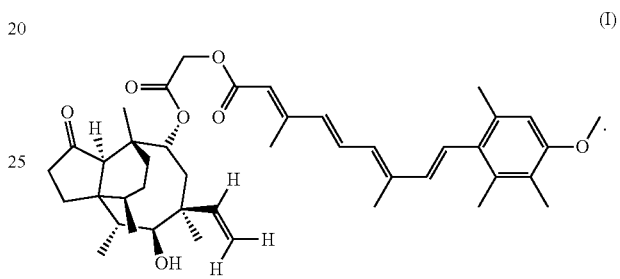

(I)

2. A method of preparing the compound of formula (I) of claim 1, comprising: reacting a compound of formula (II) with a compound of formula (III) to obtain the compound of formula (I):

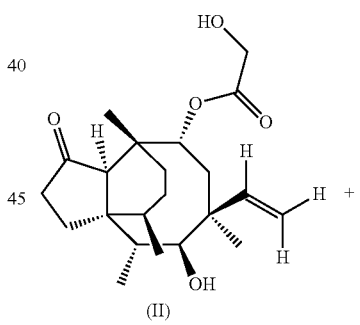

(II)

TABLE 1

| | Minimum bacteriostatic concentration of test compounds and positive controls ($\mu g \cdot mL^{-1}$) | | | | | | | |
|---|---|---|---|---|---|---|---|---|
| | MRSA | | VRE | | MDR-PA | | CR-AB | |
| | Strain | | | | | | | |
| Sample | 18-222 | 18-575 | 18-80 | 18-94 | 18-174 | 18-202 | 18-183 | 18-560 |
| Pleuromulin acitretinester | >128 | 64 | >128 | >128 | >128 | 128 | >128 | >128 |
| Gentamicin | 128 | 2 | 0.0625 | >128 | 0.0625 | 0.0625 | >128 | >128 |
| Cefazolin sodium | >128 | >128 | 32 | >128 | 8 | 128 | >128 | >128 |
| Ceftriaxone sodium | >128 | >128 | 8 | >128 | 128 | 16 | >128 | >128 |
| Pleuromulin | >128 | >128 | >128 | >128 | >128 | >128 | >128 | >128 |
| Acitretin | >128 | >128 | >128 | >128 | >128 | >128 | >128 | >128 |

-continued

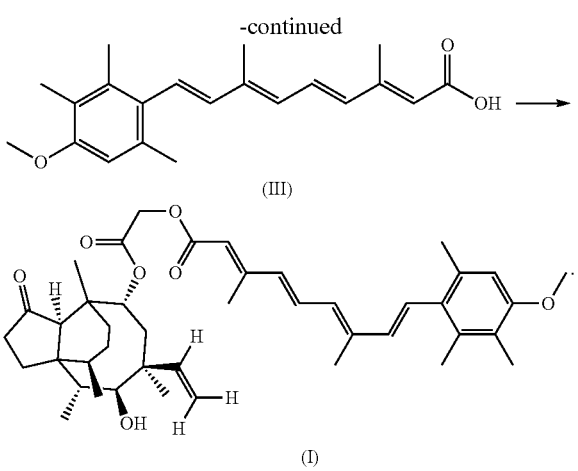

3. The method of claim 2, wherein the reaction of the compound of formula (II) with the compound of formula (III) comprises the following steps:
  placing the compound of formula (II) and the compound of formula (III), in a molar ratio of 1:1 to 1:1.3, in a reactor;
  adding an organic solvent and a catalytic amount of 4-DMAP under nitrogen atmosphere to obtain a reaction mixture;
  heating the reaction mixture at 20-40° C. for 4-8 hours;
  concentrating the reaction mixture and extracting with ethyl acetate to obtain a crude product; and
  purifying the crude product on a silica gel fresh chromatography column with petroleum ether and ethyl acetate as an eluent to obtain the compound of formula (I).

4. The method of claim 3, wherein the organic solvent is toluene, dichloromethane or acetonitrile.

5. The method of claim 4, wherein the organic solvent is dichloromethane.

6. The method of claim 3, wherein the molar ratio of the compound of formula (II) and the compound of formula (III) is 1:1.2.

7. The method of claim 3, wherein the reaction mixture is heated at 30° C.

8. The method of claim 3, wherein the reaction mixture is heated for 5 hours.

9. The method of claim 2, wherein the reaction of the compound of formula (II) with the compound of formula (III) comprises the following steps:
  placing the compound of formula (II), a catalyst, and an ionic liquid in a reactor under nitrogen atmosphere, the catalyst being 12-molybdosilicic acid hydrate ($H_6Mo_{12}O_{41}Si$);
  adding the compound of formula (III) to the reactor to form a reaction mixture;
  heating the reaction mixture at 20-60° C. for 4-10 hours;
  placing the reaction mixture in a separating funnel to separate a crude product;
  purifying the crude product by recrystallization in methanol to obtain the compound of formula (I); and
  recycling the ionic liquid.

10. The method of claim 9, wherein the ionic liquid is 1-ethyl-3-methylimidazolium tetrachloroferrate, 1-hexyl-3-methylimidazolium tetrafluoroborate or 1-n-butyl-3-methyl-imidazolium hydrogen sulfate.

11. The method of claim 10, wherein the ionic liquid is 1-n-butyl-3-methyl-imidazolium hydrogen sulfate.

12. The method of claim 9, wherein the compound of formula (II) and the compound (III) have a molar ratio of 1:1 to 1:1.3.

13. The method of claim 12, wherein the molar ratio of the compound of formula (II) and the compound of formula (III) is 1:1.1.

14. The method of claim 9, wherein the reaction mixture is heated at 40° C.

15. The method of claim 9, wherein the reaction mixture is heated for 8 hours.

* * * * *